United States Patent
Pilkington et al.

(10) Patent No.: US 10,927,347 B2
(45) Date of Patent: Feb. 23, 2021

(54) DEVICE AND METHOD FOR BREAKING DOWN AND SIZING HARVESTED FAT

(71) Applicant: Black Tie Medical Inc., San Diego, CA (US)

(72) Inventors: Mary L. Pilkington, San Diego, CA (US); Mariano C. Riego de Dios, San Diego, CA (US)

(73) Assignee: Black Tie Medical Inc., San Diego, CA (US)

( * ) Notice: Subject to any disclaimer, the term of this patent is extended or adjusted under 35 U.S.C. 154(b) by 823 days.

(21) Appl. No.: 15/154,885

(22) Filed: May 13, 2016

(65) Prior Publication Data

US 2016/0333305 A1 Nov. 17, 2016

Related U.S. Application Data

(60) Provisional application No. 62/162,367, filed on May 15, 2015, provisional application No. 62/162,389, filed on May 15, 2015.

(51) Int. Cl.
| | |
|---|---|
| *C12N 5/077* | (2010.01) |
| *A61M 1/00* | (2006.01) |
| *C12M 1/33* | (2006.01) |

(52) U.S. Cl.
CPC .............. *C12N 5/0653* (2013.01); *A61M 1/00* (2013.01); *C12M 45/02* (2013.01)

(58) Field of Classification Search
None
See application file for complete search history.

(56) References Cited

U.S. PATENT DOCUMENTS

| | | | | |
|---|---|---|---|---|
| 604,931 | A * | 5/1898 | Eisendrath | B01D 35/02 210/445 |
| 1,888,150 | A * | 11/1932 | Walker | B01D 46/10 55/486 |
| 2,073,991 | A * | 3/1937 | Koser | B01D 29/05 210/445 |
| 2,192,968 | A * | 3/1940 | Fieser | B01D 46/10 55/486 |
| 2,665,009 | A * | 1/1954 | Harstick | B01D 29/05 210/449 |
| 2,784,843 | A * | 3/1957 | Braunlich | B01D 29/925 210/247 |
| 2,879,207 | A * | 3/1959 | Poitras | C12M 33/14 435/287.7 |
| 2,923,669 | A * | 2/1960 | Poitras | C12M 25/02 435/34 |

(Continued)

OTHER PUBLICATIONS

Tulip Product Catalog, select pages, Jan. 2014.

(Continued)

*Primary Examiner* — Robert J Popovics
(74) *Attorney, Agent, or Firm* — Rodney F. Brown

(57) ABSTRACT

A fat sizing device includes a first filter element and a second filter element. The first filter element has an exterior formed from a ceramic such as titanium nitride. The second filter element is positioned in series with the first filter element and has an exterior formed from an organic polymer such as a parylene. The first filter element has a first mesh size and the second filter element has a second mesh size different than the first mesh size and may be less than the first mesh size.

12 Claims, 4 Drawing Sheets

(56) References Cited

U.S. PATENT DOCUMENTS

| | | | | |
|---|---|---|---|---|
| 3,448,041 A * | 6/1969 | Swank | A61M 1/3679 | 210/774 |
| 3,608,735 A * | 9/1971 | Smith | E03C 1/086 | 210/449 |
| 3,658,183 A * | 4/1972 | Best | B01D 29/012 | 210/446 |
| 3,686,835 A * | 8/1972 | Strange | G01N 1/2205 | 96/417 |
| 3,782,083 A * | 1/1974 | Rosenberg | B01D 46/10 | 55/491 |
| 3,788,484 A * | 1/1974 | Godin | B01D 29/70 | 210/447 |
| 3,800,510 A * | 4/1974 | Lamond | B01D 46/0012 | 96/6 |
| 3,817,389 A * | 6/1974 | Weichselbaum | A61M 5/165 | 210/448 |
| 3,844,895 A * | 10/1974 | Rose | B01D 29/00 | 435/297.2 |
| 3,874,851 A * | 4/1975 | Wilkins | A61B 5/15003 | 422/536 |
| 3,932,153 A * | 1/1976 | Byrns | A61M 16/1055 | 55/511 |
| 3,933,652 A * | 1/1976 | Weichselbaum | A61M 5/3145 | 210/446 |
| 3,935,111 A * | 1/1976 | Bentley | B01D 29/58 | 210/446 |
| 3,952,747 A * | 4/1976 | Kimmell, Jr. | A61F 2/01 | 606/195 |
| 3,954,625 A * | 5/1976 | Michalski | B01D 29/012 | 210/445 |
| 3,972,225 A * | 8/1976 | Fort | G01N 1/2214 | 73/28.04 |
| 3,993,561 A * | 11/1976 | Swearingen | B01D 35/02 | 210/131 |
| 4,013,072 A * | 3/1977 | Jess | A61M 5/165 | 604/252 |
| 4,092,246 A * | 5/1978 | Kummer | A61M 5/165 | 210/494.1 |
| 4,111,807 A * | 9/1978 | Boomus | B01D 46/10 | 210/251 |
| 4,113,627 A * | 9/1978 | Leason | B01D 19/0031 | 210/446 |
| 4,127,131 A * | 11/1978 | Vaillancourt | A61M 5/165 | 210/448 |
| 4,136,029 A * | 1/1979 | Cosack | B01D 29/05 | 210/242.1 |
| 4,148,732 A * | 4/1979 | Burrow | A61M 16/1055 | 210/232 |
| 4,155,247 A * | 5/1979 | Kaczmarek | G01N 1/2202 | 73/863.23 |
| 4,159,954 A * | 7/1979 | Gangemi | B01D 63/087 | 210/446 |
| 4,191,654 A * | 3/1980 | Larson | A61M 5/165 | 210/451 |
| 4,225,440 A * | 9/1980 | Pitesky | B01D 61/142 | 210/321.64 |
| 4,229,306 A * | 10/1980 | Hein | B01D 29/012 | 210/446 |
| 4,306,973 A * | 12/1981 | Ishikawa | A61M 5/165 | 210/336 |
| 4,319,996 A * | 3/1982 | Vincent | A61M 5/385 | 210/188 |
| 4,362,047 A * | 12/1982 | vonReis | G01N 1/2205 | 55/503 |
| 4,404,006 A * | 9/1983 | Williams | B29C 66/30223 | 55/502 |
| 4,426,295 A * | 1/1984 | Evans | B01D 29/05 | 210/772 |
| 4,444,661 A * | 4/1984 | Jackson | B01D 29/05 | 210/446 |
| 4,453,927 A * | 6/1984 | Sinko | A61M 1/3633 | 604/513 |
| 4,459,139 A * | 7/1984 | vonReis | A61M 5/385 | 210/416.1 |
| 4,713,344 A * | 12/1987 | Markhart, III | C12M 45/02 | 210/314 |
| 4,883,507 A * | 11/1989 | Rey | A61K 9/2095 | 95/273 |
| 4,944,876 A * | 7/1990 | Miller | B01D 29/05 | 210/321.75 |
| 5,002,538 A | 3/1991 | Johnson | | |
| 5,391,298 A * | 2/1995 | Pieper | B01D 11/0415 | 210/638 |
| 5,454,951 A * | 10/1995 | Hoopman | B01D 29/05 | 210/321.84 |
| 5,766,469 A * | 6/1998 | Boast | B01D 29/012 | 210/335 |
| 5,804,366 A * | 9/1998 | Hu | A61F 2/062 | 435/1.1 |
| 5,954,961 A * | 9/1999 | Carchidi | B01D 35/02 | 210/452 |
| 6,010,627 A * | 1/2000 | Hood, III | A61K 35/14 | 210/321.6 |
| 6,015,500 A * | 1/2000 | Zuk, Jr. | B01D 63/08 | 210/767 |
| 6,342,157 B1 * | 1/2002 | Hood, III | A61K 35/14 | 210/321.6 |
| 6,346,192 B2 * | 2/2002 | Buhr | B01D 29/58 | 210/314 |
| 6,569,118 B2 | 5/2003 | Johnson et al. | | |
| 6,605,217 B2 * | 8/2003 | Buhr | B01D 61/18 | 210/335 |
| 6,627,072 B1 * | 9/2003 | Ridge | A61H 35/006 | 210/149 |
| 6,672,135 B2 * | 1/2004 | Adiletta | B01D 46/543 | 210/321.84 |
| 6,779,411 B1 * | 8/2004 | Spurgeon | G01N 1/2205 | 73/863.23 |
| 6,905,612 B2 * | 6/2005 | Dorian | B01D 15/02 | 210/219 |
| 6,966,443 B1 * | 11/2005 | Ridge | A61H 35/006 | 210/446 |
| 7,291,450 B2 * | 11/2007 | Sowemimo-Coker | A61K 35/15 | 435/2 |
| 7,306,740 B2 * | 12/2007 | Freund | A61B 17/32002 | 210/781 |
| 7,682,818 B2 * | 3/2010 | Mori | B01L 3/0275 | 422/68.1 |
| 7,744,820 B2 * | 6/2010 | Togawa | B01D 61/18 | 210/348 |
| 7,846,743 B2 * | 12/2010 | Tai | B01D 61/14 | 210/490 |
| 7,972,869 B2 * | 7/2011 | Quine | G01N 1/2214 | 422/83 |
| 8,288,170 B2 * | 10/2012 | Tai | B01D 61/14 | 210/490 |
| 8,696,674 B2 * | 4/2014 | Howard | A61B 17/1635 | 606/86 R |
| 8,770,047 B2 * | 7/2014 | Raadnui | G01N 3/56 | 494/36 |
| 8,795,194 B2 * | 8/2014 | Howard | A61B 17/1635 | 600/563 |
| 9,133,431 B2 | 9/2015 | Peterson et al. | | |
| 9,248,384 B2 * | 2/2016 | Dominguez | B01D 33/00 | |
| 9,352,021 B2 * | 5/2016 | Hanna | A61K 38/1722 | |
| 9,695,398 B2 | 7/2017 | Peterson et al. | | |
| 9,777,257 B2 * | 10/2017 | Howard | A61B 17/1635 | |
| 9,822,341 B2 * | 11/2017 | Howard | A61B 17/1635 | |
| 9,909,103 B2 * | 3/2018 | Howard | A61B 17/1635 | |
| 10,039,886 B2 * | 8/2018 | Pilkington | A61M 5/31513 | |
| 10,206,950 B2 * | 2/2019 | Sowemimo-Coker | A61K 35/15 | |
| 10,279,325 B1 | 5/2019 | Crombie | | |
| 10,478,587 B2 * | 11/2019 | Tremolada | A61M 19/00 | |
| 2004/0071668 A1 * | 4/2004 | Bays | A61F 2/00 | 424/93.7 |

(56) References Cited

U.S. PATENT DOCUMENTS

| | | | |
|---|---|---|---|
| 2004/0182788 A1* | 9/2004 | Dorian | B01D 15/02 210/649 |
| 2004/0245163 A1* | 12/2004 | Lim | B01D 61/18 210/323.1 |
| 2005/0124073 A1* | 6/2005 | Freund | A61B 17/32002 436/177 |
| 2005/0135973 A1* | 6/2005 | Quine | G01N 1/2214 422/504 |
| 2005/0205498 A1* | 9/2005 | Sowemimo-Coker | A61K 35/15 210/782 |
| 2008/0243028 A1* | 10/2008 | Howard | A61B 17/1635 600/565 |
| 2009/0152098 A1* | 6/2009 | Hooper | A61M 5/002 204/176 |
| 2011/0020224 A1* | 1/2011 | Piazzi | A61K 51/1045 424/1.69 |
| 2011/0244443 A1* | 10/2011 | van Rijn | B01D 63/087 435/2 |
| 2012/0045424 A1* | 2/2012 | Esteron | A61K 35/16 424/93.72 |
| 2012/0118825 A1* | 5/2012 | Margraf | B01D 63/087 210/645 |
| 2014/0127745 A1* | 5/2014 | Gonzaga | G01N 1/30 435/40.51 |
| 2014/0190888 A1* | 7/2014 | van Rijn | A61M 1/3633 210/651 |
| 2014/0275497 A1* | 9/2014 | Leach | A61K 38/1793 530/427 |
| 2014/0308742 A1* | 10/2014 | Howard | A61B 17/1635 435/325 |
| 2014/0309652 A1* | 10/2014 | Howard | A61B 17/1635 606/115 |
| 2014/0322743 A1* | 10/2014 | Tang | B01D 29/00 435/29 |
| 2014/0360944 A1* | 12/2014 | Esteron | A61K 35/14 210/698 |
| 2015/0025223 A1* | 1/2015 | Esteron | C07K 14/545 530/351 |
| 2015/0093362 A1* | 4/2015 | Dominguez | A61L 27/3683 424/93.7 |
| 2015/0101995 A1* | 4/2015 | Kim | A61M 1/3496 210/787 |
| 2015/0164949 A1* | 6/2015 | Sowemimo-Coker | A61K 35/15 424/93.7 |
| 2016/0333305 A1* | 11/2016 | Pilkington | C12N 5/0653 |
| 2017/0368226 A1* | 12/2017 | Pilkington | C12M 45/02 |
| 2018/0303983 A1* | 10/2018 | Goisis | A61M 1/029 |

OTHER PUBLICATIONS

Alexander, Robert W., "Understanding Mechanical Emulsification vs. Enzymatic Isolation of tSVF From Adipose Tissue", Journal of Prolotherapy, 8:e947-e960, Feb. 2016.

Tonnard, Patrick, et al., "Nanofat Grafting: Basic Research and Clinical Applications", Plastic and Reconstructive Surgery Journal, v. 132(4), at pp. 1017-1026, Oct. 2013.

* cited by examiner

DEVICE AND METHOD FOR BREAKING DOWN AND SIZING HARVESTED FAT

This a non-provisional patent application claiming the priority of Provisional Patent Application Ser. No. 62/162,367 and 62/162,389, both filed on May 15, 2015, which are incorporated herein by reference.

BACKGROUND OF THE INVENTION

The present invention relates generally to plastic surgery, more particularly to cosmetic surgery and still more particularly to fat transfer.

Fat transfer, also known as fat grafting, entails two procedures performed in series. In the first fat transfer procedure known as fat harvesting, fat is removed and recovered from one or more fatty sites on the body of a patient, such as the thighs or stomach, by any number of techniques including liposuction or lipoplasty. The harvested fat is a complex, multi-component mixture comprised of mature adipocytes, precursor adipocytes, other precursor cells and lipids from ruptured mature adipocytes. Adipocytes are the primary cells in adipose tissue, which is the loose connective tissue in the body where most fat resides. As connective tissue, adipose tissue also includes fibers, fiber fragments and other non-fat material in addition to the adipocytes. Lipids are molecules including fat molecules which may be simplistically characterized as loose fat or fat particles. Harvested fat may be categorized by size as macrofat, microfat or nanofat in descending order of particle size.

In the second fat transfer procedure known as fat re-injection, the harvested fat is re-injected into the body of the same patient, but into one or more different sites on the body from where the fat was harvested. The re-injected fat increases volume at the treated re-injection site and enhances the appearance of the patient. Potential re-injection sites include the face, breasts, cheeks, lips, buttocks, and chin.

Nanofat, as compared to larger fats, has been found to be more desirable for fat re-injection because it produces markedly better results in the ultimate appearance of the patient, particularly when treating superficial dermal layers such as eyelids and the like. Fat transfer practitioners have also found it highly advantageous to use very fine sharp syringe cannulas on the order of about 27-30 gauge when re-injecting harvested fat. The fine cannulas are less invasive and disruptive to the patient and can substantially reduce pain, bruising and/or other undesirable side effects of the procedure while simultaneously shortening patient recovery time. Nanofat, as compared to larger fats, does not substantially clog or otherwise impede flow through these very fine cannulas, thereby additionally rendering nanofat more desirable for fat re-injection. An exemplary fat transfer procedure using nanofat is described in "Nanofat Grafting: Basic Research and Clinical Applications," Tonnard, Patrick, et al., *Plastic and Reconstructive Surgery Journal*, v. 132(4), at pp. 1017-26, October 2013, which is incorporated herein by reference. A shortcoming of the above-recited fat transfer procedure, however, is that the procedure is performed using an essentially open, aerobic system.

In view of the above it is desirable to break down and size the harvested fat before re-injecting the fat into the body. More particularly, it is desirable to separate oversize particles from the harvested fat to produce a purer smaller particle size composition of nanofat from the harvested fat for re-injection.

The present invention recognizes a need for a device and method for breaking down and sizing harvested fat. In particular, the present invention recognizes a need for a closed, anaerobic device and method for effectively and efficiently breaking down and sizing harvested fat. More particularly, the present invention recognizes a need for a device and method which breaks down harvested fat into smaller particle sizes and separates the smaller particle size loose fat from the remaining oversized materials in the harvested fat. The present invention further recognizes a need for a device and method which preferably recovers the smaller particle size emulsion of loose fat, preferably in the form of nanofat, which is eminently suited for injecting into the patient in the re-injection procedure while disposing or otherwise discarding the oversized materials.

Accordingly, it is an object of the present invention to satisfy all of the above-recited needs. As such, it is an object of the present invention to provide a device and method for breaking down and sizing harvested fat. More particularly, it is an object of the present invention to provide a device and method which effectively and efficiently breaks down adipose tissue in the harvested fat after the harvested fat is withdrawn from one site in the body and produces a smaller particle size emulsion of loose fat, preferably nanofat, for re-injection into another site in the body. More particularly still, it is an object of the present invention to provide a device and method which breaks down and sizes harvested fat in an essentially closed, anaerobic system. These objects and others are accomplished in accordance with the invention described hereafter.

SUMMARY OF THE INVENTION

The present invention may be characterized as a fat sizing device including a filter housing, a filter element, an inlet coupler and an outlet coupler. The filter housing has an inlet, an outlet and a housing passageway extending between the inlet and outlet. The filter element is positioned within the housing passageway. The inlet coupler is positioned at the inlet and adapted to couple with a discharging syringe containing a harvested fat. The outlet coupler is positioned at the outlet and adapted to couple with a receiving syringe for receiving a sized fat emulsion.

In accordance with one embodiment, the filter element is a first filter element and the fat sizing device further comprises a second filter element positioned within the housing passageway. The first filter element and second filter element are preferably positioned in series within the housing passageway. In accordance with another embodiment, the first filter element has an exterior formed from a first material that is different from a second material that forms an exterior of the second filter element. The first material may preferably be a ceramic and the second material may preferably be an organic polymer. In accordance with another embodiment, the first filter element has a first mesh size and the second filter element has second mesh size different than the first mesh size.

The present invention may be alternately characterized as a fat sizing device including a first filter element and a second filter element. The first filter element has an exterior formed from a ceramic. The ceramic may preferably be titanium nitride. The second filter element is positioned in series with the first filter element and has an exterior formed from an organic polymer. The organic polymer may preferably be a parylene. In accordance with one embodiment, the first filter element has a first mesh size and the second filter element has a second mesh size different than the first mesh size. The first mesh size may preferably be greater than the second mesh size.

The present invention may be alternately characterized as a method for removing unwanted materials from a harvested fat. The harvested fat is passed through a first filter element having an exterior formed from a first material to separate out first unwanted materials and obtain a first fat filtrate. The first fat filtrate is passed through a second filter element having an exterior formed from a second material different than the first material to separate out second unwanted materials and obtain a second fat filtrate which is recovered. The second fat filtrate may preferably be a nanofat. In accordance with one embodiment, the harvested fat passed through the first filter element is an at least partially emulsified harvested fat. The at least partially emulsified harvested fat is formed by passing raw harvested fat through a flow restrictor to at least partially emulsify the raw harvested fat.

The present invention will be further understood from the drawings and the following detailed description.

BRIEF DESCRIPTION OF THE SEVERAL VIEWS OF THE DRAWINGS

The below-listed drawing figures illustrate one or more embodiments of the present invention by way of example and not by way of limitation. Common reference characters may be used among the different drawing figures to indicate the same or similar structural elements.

DETAILED DESCRIPTION OF THE INVENTION

Figure 1:
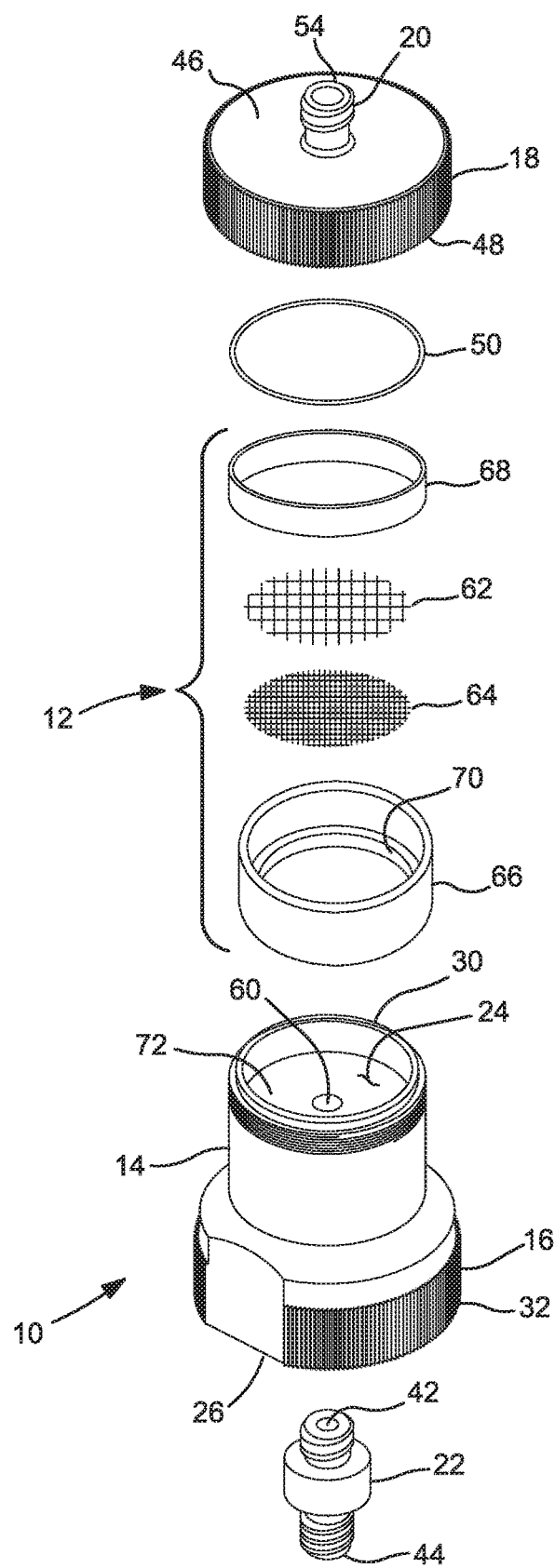
FIG. 1 is an exploded view of an embodiment of a fat sizing device.
Figure 2:
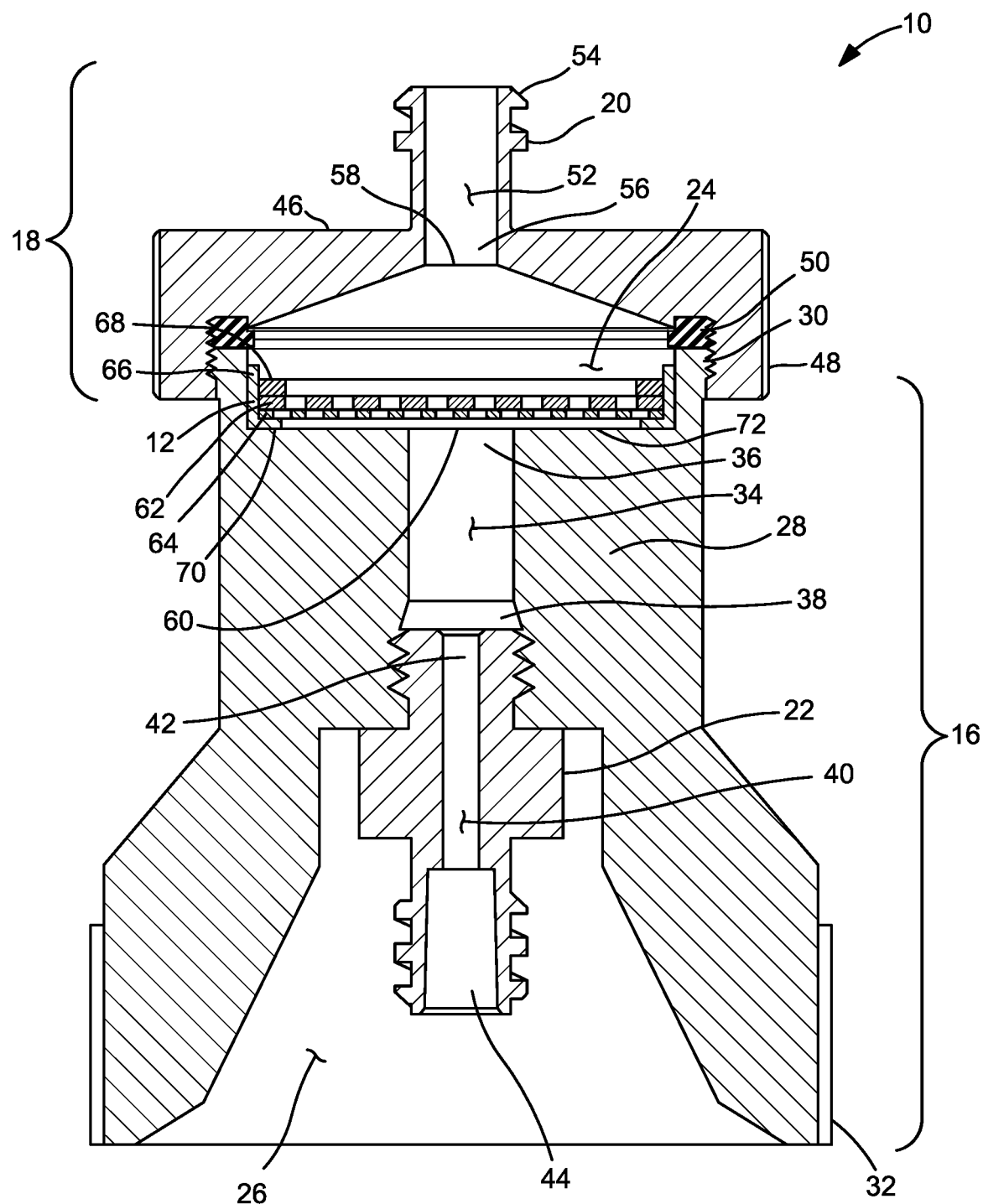
FIG. 2 is a cross section of the fat sizing device shown in FIG. 1.

FIGS. 1 and 2 show an embodiment of a fat sizing device which is generally designated 10. The relative positional terms upper and lower are generally used herein, unless stated or implied otherwise, to describe the positioning of various elements of the fat sizing device 10 relative to one another when the fat sizing device 10 is in its usual operative orientation. The relative positional terms inner or inside and outer or outside are generally used herein, unless stated or implied otherwise, to describe the positioning of various elements of the fat sizing device 10 relative to the central longitudinal axis of the fat sizing device 10 when the fat sizing device 10 is in its usual operative orientation.

The fat sizing device 10 includes a cartridge, alternately termed a filter cartridge or sieve cartridge, 12 contained within a housing 14. The housing 14 comprises a base 16, a cover 18, a first connection member 20 and a second connection member 22. The housing 14 is formed from a material which preferably exhibits one or more of the following desirable characteristics and which more preferably exhibits all of the following desirable characteristics: durable, strong, rigid, wear-resistant, non-corrosive, smooth, non-porous, and substantially inert. As such, the surface of the housing 14 preferably does not readily retain contaminants during use. In accordance with one embodiment, the housing 14 is formed from a material having the above-recited characteristics which is suitable for autoclaving to enable sterilization and reuse of the housing 14 an indefinite number of times. Exemplary materials of construction for a reusable housing 14 include heat-resistant cast metals and the like, such as aluminum or stainless steel. Alternatively, the housing 14 is formed from a sterile, single-use, disposable material such as a plastic, which likewise has the above-recited characteristics.

The base 16 is generally cylindrically shaped with a hollowed out interior which is separated into two chambers 24, 26 by a divider 28. The first or upper chamber 24, alternately termed a filtration chamber or sieve chamber, has a tube-like shape with a chamber first end, a chamber second end and a chamber sidewall extending continuously from the chamber first end to the chamber second end. The first chamber 24 extends into a first or upper portion of the base 16 from an open circular first or upper end 30 of the base 16. As such, the inside and outside diameters of the first chamber 24 are preferably substantially equal to those of the first end of the base 16. An exemplary first chamber has an inside diameter on the order of about 1", an outside diameter on the order of about 1⅛" and a depth on the order of about ¼". The second or lower chamber 26 extends into a second or lower portion of the base 16 from an opposite second or lower end 32 of the base 16. The outside surface of the second end 32 is knurled to facilitate gripping it. The divider 28 extends across the inside diameter at a middle portion of the base 16 between the first and second portions. The divider 28 has an open divider passageway 34 which is a circular opening providing a continuous tube-like fluid flowpath extending through the middle portion of the base 16. The divider passageway 34 is centrally longitudinally aligned with the central longitudinal axis of the base 16. In accordance with the present embodiment, the divider passageway 34 has a first or upper end 36 which is smooth and an opposite second or lower end 38 which is provided with female threads on its inside surface.

The second or lower connection member 22 has a tube configuration with an open second connection passageway 40 which provides a continuous fluid flowpath centrally longitudinally extending through the second connection member 22. The second connection passageway 40 extends from a first or upper end 42 of the second connection member 22 to an opposite second or lower end 44 of the second connection member 22. The first end 42 of the second connection member 22 is provided with male threads on its outside surface which are sized in correspondence the female threads in the second end 38 of the divider passageway 34. Accordingly, the first end 42 of the second connection member 22 is threadably received within the second end 38 of the divider passageway 34 and releasably retained therein, thereby releasably attaching the second connection member 22 to the base 16. The second end 44 of the second connection member 22, termed a housing outlet for a fat sizing device filtrate, is preferably fitted with an outlet coupler, and more preferably, a Luer coupler for coupling a syringe or some other like device to the second end 44 of the second connection member 22. When the first end 42 of the second connection member 22 is retained in the second end 38 of the divider passageway 34, the second end 44 of the second connection member 22 extends into the second chamber 26 where the second end 44 is exposed to the external environment and readily accessible to a user of the fat sizing device 10.

The cover 18 is essentially a screw-on top or lid which is sized to fit over the first end 30 of the base 16. When the fat sizing device 10 is in its usual operative orientation the cover 18 is positioned atop the fat sizing device 10 and the base 16 is positioned below the cover 18. The cover 18 has a circular enclosing surface 46 from which a short tubular sealing lip 48 extends that is aligned circumferentially orthogonal to the enclosing surface 46. The outside surface of the sealing lip 48 is knurled to facilitate gripping it. The sealing lip 48 is provided with female threads on its inside surface and the first end 30 of the base 16 is provided with corresponding male threads on its outside surface. The inside diameter of the sealing lip 48 is preferably substantially equal to (i.e., equal to or at most only slightly greater than) the outside diameter of the first end 30 of the base 16. Accordingly, the first end 30 of the base 16 is threadably received within the sealing lip 48 and releasably retained therein, thereby releasably attaching the cover 18 to the base 16. The housing 14 may also include a sealing element 50, such as an o-ring which is at least somewhat pliant and compressible. The sealing element 50 substantially prevents fluid leakage at the junction of the base 16 and cover 18 when they are attached to one another.

The first or upper connection member 20 is preferably integrally formed with the enclosing surface 46 of the cover 18 at its center. The first connection member 20 has a tube configuration with an open first connection passageway 52 extending through its entirety, thereby providing a continuous central longitudinal fluid flowpath. In particular, the first connection passageway 52 extends from a first or upper end 54 of the first connection member 20 to an opposite second or lower end 56 of the first connection member 20. The first end 54 of the first connection member 20, termed a housing inlet for a fat sizing device feed, is preferably fitted with an inlet coupler, and more preferably, a Luer coupler for coupling a syringe or some other like device to the first end 54 of the first connection member 20. The first end 54 extends away from the base 16 in a manner which exposes the Luer coupler to the external environment and renders it readily accessible to a user of the fat sizing device 10 while the first connection passageway 52 opens directly into the first chamber 24 at the second end 56 of the first connection member 20 when the cover 18 is retained on the base 16. Retention of the cover 18 on the base 16 also substantially encloses the first chamber 24. As such, access to the enclosed first chamber 24 is essentially limited to a chamber inlet 58 and a chamber outlet 60. The chamber inlet 58 is positioned at the first end of the sieve chamber 24 and is synonymous with the opening of the first connection passageway 52 at the second end 56 of the first connection member 20. The chamber outlet 60 is positioned at the second end of the sieve chamber 24 and is synonymous with the opening of the divider passageway 34 at its first end 36. It is apparent from the above that the first connection passageway 52, first chamber 24, divider passageway 34 and second connection passageway 40 are aligned in series in fluid communication with one another and, in sum, provide a continuous open longitudinal fluid passageway or flowpath through the entirety of fat sizing device 10 when the base 16, cover 18, and second connection member 22 are interconnected to form the assembled housing 14. This passageway is termed the housing passageway or alternately the fat flowpath.

The filter cartridge 12 is comprised of a first filter element 62, a second filter element 64, a filter element mount 66 and a filter element retention member 68. It is noted that the present embodiment of the fat sizing device 10 having two filter elements 62, 64 is shown and described herein as a preferred example and not by way of limitation. The present invention generally encompasses a fat sizing device having at least one filter element. Thus, the number of filter elements having utility in a fat sizing device is within a range from one up to two or more. The upper limit of this range is subject to physical and operational limits readily ascertainable and/or within the purview of a skilled artisan applying the teaching herein. Nevertheless, a preferred upper limit for the number of filter elements in the present fat sizing device is four.

The filter element mount 66 and filter element retention member 68 both have ring configurations and are both preferably formed from a disposable rigid or semi-rigid plastic. The outside diameters of the filter element retention member 68 and first and second filter elements 62, 64 are preferably equal to one another and substantially equal to (i.e., equal to or at most only slightly less than) the inside diameter of the filter element mount 66 so that the filter element retention member 68 and first and second filter elements 62, 64 snugly nest within the filter element mount 66 when the filter cartridge 12 is assembled as described below. The inside edge of the filter element mount 66 has a circumferential ledge 70 integrally formed with the edge. The ledge 70 has a substantially smaller inside diameter than the outside diameters of filter element retention member 68 and first and second filter elements 62, 64 so that the ledge 70 securely retains the filter element retention member 68 and first and second filter elements 62, 64 when they are nested in the filter element mount 66.

Each of the first and second filter elements 62, 64 is preferably a disc-shaped screen in the form of a sieve having a lattice or grid structure. The first and second filter elements 62, 64 are very thin, i.e., have a very small thickness relative to the other components of the fat sizing device 10. Although the present invention is not limited to any specific geometric configuration of the screen openings for the filter elements, the present first and second filter elements 62, 64 have essentially square-shaped openings. In the case where the fat sizing device has only two filter elements, as in the present embodiment, each filter element preferably has a different mesh size than the other and is preferably formed from a different material than the other. In the case where the fat sizing device has more than two filter elements, at least two of the filter elements in the fat sizing device preferably have different mesh sizes from one another and are preferably formed from different materials than one another.

The first and second filter elements 62, 64 are preferably selected to have mesh sizes within a range of about 100 microns to about 1000 microns. In a preferred configuration of the fat sizing device 10, the first filter element 62 is alternately termed an inlet filter element because it is more proximal to the chamber inlet 58 than is the second filter element 64. The second filter element 64 is alternately termed an outlet filter element because it is more proximal the chamber outlet 60 than is the first filter element 62. In this preferred configuration, the inlet filter element 62 has a larger mesh size than the outlet filter element 64. For example, the inlet filter element 62 of the present embodiment has a preferred mesh size of 600 microns and the outlet filter element 64 has a preferred mesh size of 400 microns, although it is understood that filter elements having any mesh size within the above-recited range are within the scope of the present invention.

As recited above, each of the filter elements 62, 64 is made up of a different material and both filter elements are preferably formed from sterile, disposable, single-use materials. In the present embodiment, the inlet filter element 62 is preferably formed from two components, namely, an interior substrate and an exterior coating which preferably continuously coats the substrate. A preferred substrate is an inert stainless steel. A preferred coating is a hard material which has sharp surface edges and which is chemically inert with harvested fat. A preferred coating material exhibiting these desired properties may be selected from hard, wear-resistant, high-strength, inorganic ceramics typically having a crystalline structure. An exemplary preferred material is titanium nitride which has been found to be an effective coating for filtering unwanted material including large particle size fat out of the harvested fat.

In the present embodiment, the outlet filter element 64 is likewise preferably formed from two distinct components, a substrate and a coating which preferably continuously coats the substrate. A preferred substrate is likewise an inert stainless steel. However, a preferred coating is formed from a smoother, more lubricious, low friction material having softer more rounded surface edges than the coating of the inlet filter element 62. A preferred coating material exhibiting these desired properties which is also chemically inert with harvested fat may be selected from polymeric materials. An exemplary preferred material is selected from a class of organic polymers generally known as parylenes which can be coated onto the substrate by vapor deposition. Parylene is the generic name for members of a unique polymer series. The basic member of the series, called Parylene N, is poly-para-xylylene, a completely linear, highly crystalline, lubricious material. The outlet filter element 64 has been found to be particularly effective when it is coated with a parylene and positioned downstream of the inlet filter element 62 coated with titanium nitride. Placing these two different sized and different composition filter elements in series is believed to achieve a significant degree of synergy in effectively and efficiently removing unwanted large particle size materials from the harvested fat while retaining desirable nanofat consisting essentially of smaller loose fat particles in the filtrate when the harvested fat is passed through the fat sizing device 10.

Although the present invention is not limited to any particular filtration mechanism, it is believed that the filtration mechanism is primarily physical and does not substantially rely on chemical adsorption. In particular, the inlet filter element 62 is believed to rely inter alia on the coarse sharp-edged surface of the titanium nitride to effectively and efficiently physically snag unwanted larger fiber fragments and fat particles found in harvested fat upon contact with its surface when the harvested fat is being passed through the fat sizing device 10 to produce a desirable nanofat emulsion as the filtrate. In contrast, the smooth-surfaced outlet filter element 64 is believed to rely almost entirely on its relatively smaller mesh size openings to physically exclude unwanted larger particle size materials in the harvested fat from passing through the fat sizing device 10 and finding their way into the filtrate.

The inlet and outlet filter elements 62, 64 are assembled in the filter cartridge 12 by inserting the outlet filter element 64 into the interior of the filter element mount 66 until the outlet filter element 64 is firmly seated against the ledge 70 and interior circumferential walls of the filter element mount 66. The inlet filter element 62 is then inserted into the interior of the filter element mount 66 and stacked directly on top of the outlet filter element 64 with the two filter elements 62, 64 abutting and engaging one another and with the inlet filter element 62 firmly seated against the outlet filter element 64 and interior circumferential walls of the filter element mount 66. Once the filter elements 62, 64 are in place within the filter element mount 66, the filter element retention member 68 is inserted into the interior of the filter element mount 66, stacked directly atop the inlet filter element 62 and attached to the filter element mount 66, preferably by substantially permanent attachment means, such as light sensitive glue cured with UV light or the like.

The filter cartridge 12 is assembled within the housing 14 by unscrewing the cover 18 from the base 16. The outside diameters of the filter element mount 66 and correspondingly the filter cartridge 12 are preferably equal to one another and substantially equal to (i.e., equal to or at most only slightly less than) the inside diameter of the first chamber 24. Accordingly, the assembled filter cartridge 12 is inserted into the interior of the first chamber 24 until the bottom of the filter element mount 66 and correspondingly the filter cartridge 12 rest against the first or upper circular face 72 of the divider 28 which corresponds to the chamber second end. Once the filter cartridge 12 is securely seated in the first chamber 24 against the first face 72 of the divider 28 and the interior circumferential chamber sidewall, the base 16 and cover 18 are screwed back together and the fat sizing device 10 is in a condition for operation.

Although not shown, it is also within the scope of the present invention to reverse the positions of the first and second filter elements 62, 64 so that the first filter element 62 having the above recited preferred characteristics is the outlet filter element and the second filter element 64 having the above recited preferred characteristics is the inlet filter element.

Figure 3:
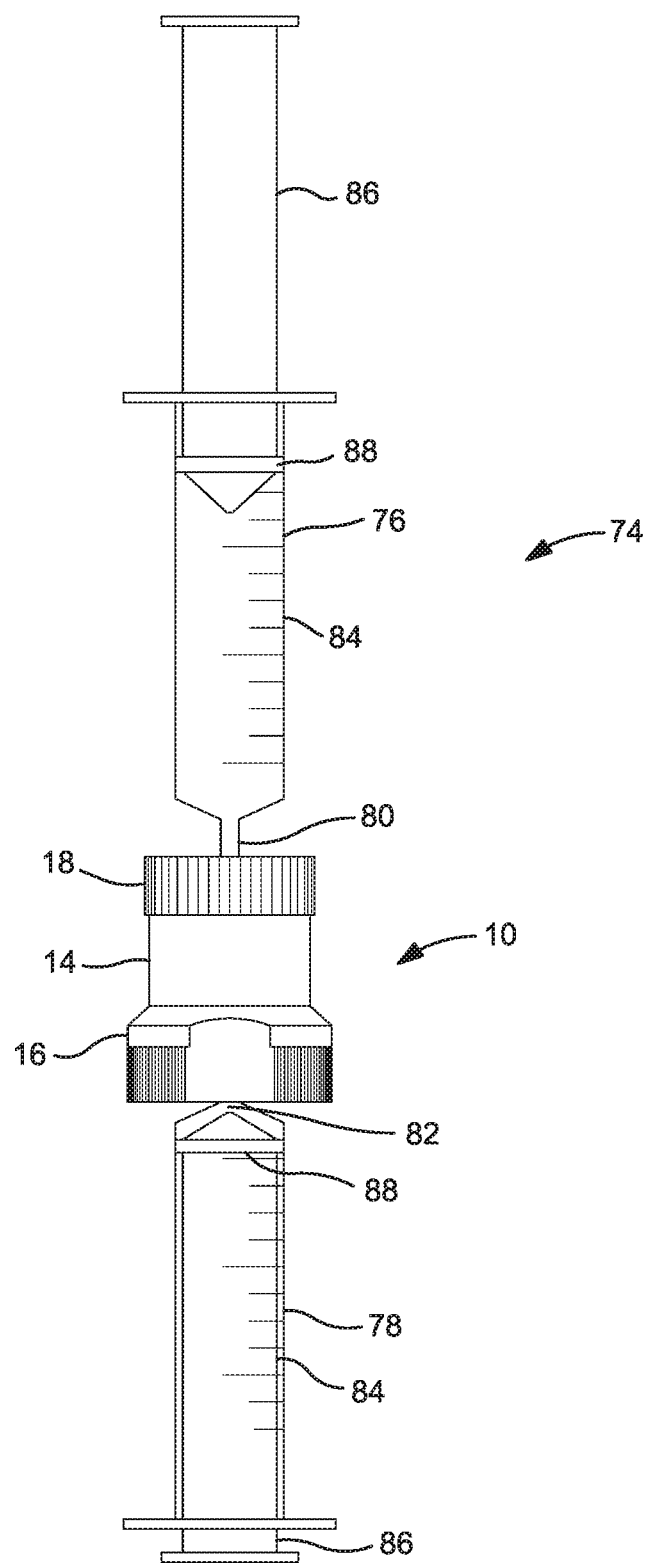
FIG. 3 is an assembled view of an embodiment of a fat sizing system which includes the fat sizing device shown in FIG. 1.

An embodiment of a method for performing a fat sizing procedure employs a fat sizing system shown in FIG. 3 and generally designated 74. The fat transfer system 74 is a closed, anaerobic system which is comprised of the above-described fat sizing device 10, a first reservoir 76 termed a discharging reservoir and a second reservoir 78 termed a receiving reservoir. The fat sizing device 10, first reservoir 76 and second reservoir 78 are all preferably initially in a sterile condition. The first reservoir 76 has a discharge connection member 80, preferably in the form of a Luer coupler, which the user releasably connects to the Luer coupler on the first end 54 of the first connection member 20 of the fat sizing device 10. The second reservoir 78 has a receipt connection member 82 likewise preferably a Luer coupler which the user releasably connects to the Luer coupler on the second end 44 of the second connection member 22 of the fat sizing device 10. The cooperative Luer couplers facilitate leak-free connection of the fat sizing device 10 to the first and second reservoirs 76, 78.

The first and second reservoirs 76, 78 of the present embodiment are preferably substantially the same although they may vary from one another with respect to fluid capacity. A preferred first and second reservoir 76, 78 is a conventional off-the-shelf, sterile, disposable, single-use syringe. An exemplary syringe having utility herein includes a barrel 84, a plunger 86 and a stopper 88. It is noted that conventional syringes also include a dispensing tip including a cannula (not shown) which removably attaches to the discharge or receipt connection member 80, 82 integral with the end of the barrel 84. In the present embodiment, however, the dispensing tip has been removed from the discharge and receipt connection members 80, 82 at the end of the barrel 84 when the syringes are utilized as the first and second reservoirs 76, 78 in the present fat sizing system 74, thereby freeing up the discharge and receipt connection members 80, 82.

Before connecting the first and second reservoirs 76, 78 to the fat sizing device 10, it is optional, but preferable, to initiate the present method by priming the fat sizing device 10 to eliminate air from the fat sizing device 10. Optional priming is effected by connecting a sterile priming reservoir (not shown) containing a suitable sterile priming fluid to the fat sizing device 10. The priming reservoir is preferably a syringe similar to or the same as the syringes used as the first and second reservoirs 76, 78. As such, the priming reservoir has a discharge connection member with a Luer coupler which is connected to the Luer coupler on the first end 54 of the first connection member 20 of the fat sizing device 10. Once the priming reservoir is connected to the fat sizing device 10, the user maintains the second end 44 of the second connection member 22 open and turns the fat sizing device 10 upside down so that the cover 18 is on the bottom and the base 16 is at the top of the fat sizing device 10. The user discharges a sufficient quantity of priming fluid from the priming reservoir into the housing passageway via the first connection member 20 to substantially fill the housing passageway as evidenced by a droplet of priming fluid appearing at the second end 44 of the second connection member 22, thereby essentially completing the priming of the fat sizing device 10.

After priming the fat sizing device 10, the user connects the second reservoir 78 to the second end 44 of the second connection member 22 as described above. The second reservoir 78 is preferably initially totally empty, i.e., does not contain any harvested fat and is also preferably devoid of any other contents. The user then turns the fat sizing device 10 right side up so that the cover 18 sits atop the fat sizing device 10. The first reservoir 76 is provided to the user which has either been pre-filled with harvested fat or has been filled by the user with harvested fat which is the feed for the fat sizing device 10. The term "filled" as used herein means that the first reservoir 76 is either at full capacity or partial capacity with harvested fat. In either case, the first reservoir 76 provided to the user contains harvested fat and, more preferably, the harvested fat is the sole content of the first reservoir 76. The user disconnects the priming reservoir from the upwardly aligned first end 54 of the first connection member 20 and connects the filled first reservoir 76 thereto.

Once the first and second reservoirs 76, 78 are connected to the fat sizing device 10, the user applies a pressurizing force to the harvested fat contained in the first reservoir 76 by depressing the plunger 86 into the barrel 84 of the syringe which drives the harvested fat from the first reservoir 76 into the housing passageway via the housing inlet, i.e., the first end 54 of the first connection member 20. More particularly, the pressurizing force drives the harvested fat through the first connection passageway 52 and the first chamber 24 of the housing passageway and, still more particularly, the pressurizing force drives the harvested fat across the inlet and outlet filter elements 62, 64 in the first chamber 24 in series. The inlet filter element 62 separates out first unwanted materials from the harvested fat and discharges a first filtrate consisting of the harvested fat absent these first unwanted materials. The first filtrate is immediately driven through the adjacent outlet filter element 64 which separates out second unwanted materials from the first filtrate and discharges a second filtrate consisting of the first filtrate absent these second unwanted materials.

The resulting desirable second filtrate, which is preferably a sized fat emulsion consisting essentially of nanofat, exits the first chamber 24 via the chamber outlet 60 and is conveyed through the housing passageway and, more particularly, through the divider and second connection passageways 34, 40 to the housing outlet, i.e., the second end 44 of the second connection member 22, where the filtrate is discharged and collected in the second reservoir 78, causing the plunger 86 to extend from the barrel 84 of the syringe. Once the first reservoir 76 is totally emptied and/or the second reservoir 78 is filled to capacity, the first and second reservoirs 76, 78 are disconnected fat sizing device 10 and the fat sizing procedure is completed. The present fat sizing procedure is preferably a single-pass procedure so that the filtrate requires no subsequent additional passes through the filter cartridge 12 beyond the first pass described above.

Upon completion of the fat sizing procedure, the filter cartridge 12 is disassembled from the housing 14 by unscrewing the cover 18 from the base 16. The used sealing element 50 is removed from the cover 18 and the spent or first filter cartridge 12 which contains the filter cake is removed from the first chamber 24. The filter cake preferably consists essentially of the first and second unwanted materials including larger fat particles and solids. The disassembled housing 14 is preferably sterilized by autoclaving for reuse in the fat sizing device 10 with a new filter cartridge 12 and sealing element 50. The used sealing element 50 and spent filter cartridge 12 are preferably not reused beyond a single use. Instead the sealing element 50, spent filter cartridge 12 and unwanted filter cake are preferably disposed in an environmentally acceptable manner. It is noted that, in any case, each filter cartridge 12 typically has a filter capacity of about 60 cc harvested fat throughput before it becomes overloaded and must be switched out for a new or second filter cartridge 12 including third and fourth filter or sieve elements.

Figure 4:
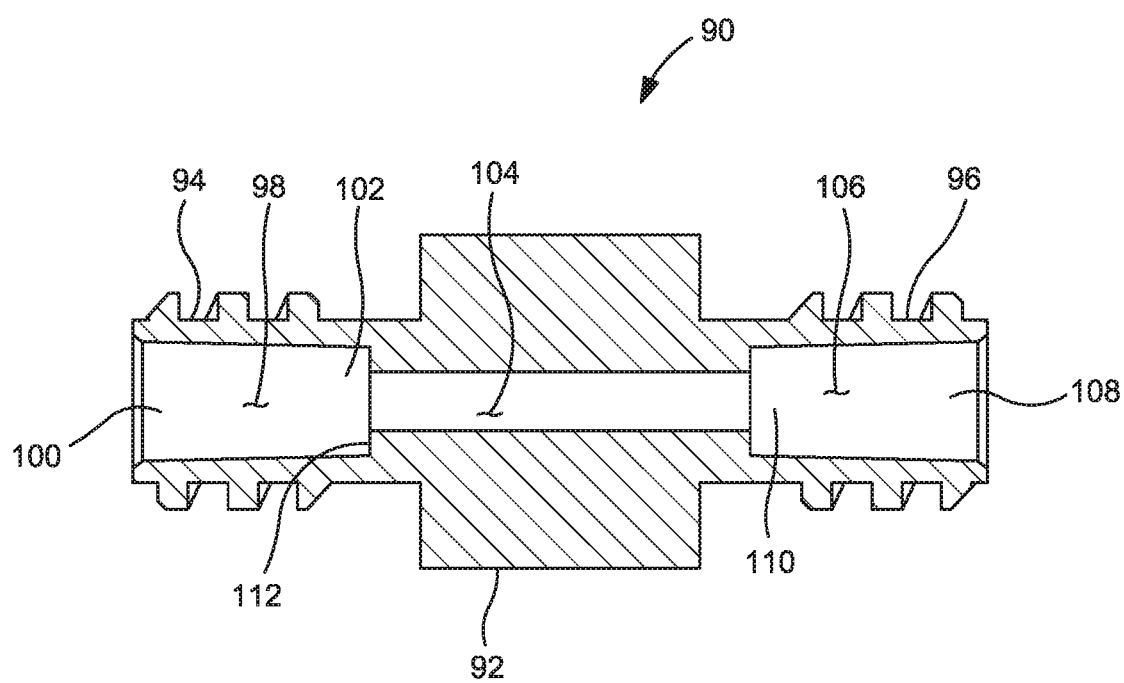
FIG. 4 is a cross section of an embodiment of an emulsification device.

An alternate embodiment of a method for performing a fat sizing procedure using a fat sizing system, such as disclosed herein, includes all of the above recited priming and filtration steps and further includes one or more prefiltration steps prior to the filtration steps. In particular, the raw unprocessed harvested fat undergoes one or more prefiltration steps prior to filtration which at least partially emulsifies the unprocessed harvested fat prior to filtration. Each prefiltration step utilizes an emulsification system, an embodiment of which is described hereafter. The emulsification system is a closed, anaerobic system which includes an emulsification device generally designated 90 in FIG. 4, a first reservoir (not shown) and a second reservoir (not shown). The emulsification device 90, first reservoir and second reservoir are all preferably initially in a sterile condition. The emulsification device 90 may be generally characterized as a flow restrictor. The emulsification device 90 comprises a cylindrically shaped body 92, a first connection member 94 at one end of the body 92 and a second connection member 96 at the opposite end of the body 92. The first and second connection members 94, 96 are preferably integrally formed with the body 92. As such, the body 92 and first and second connection members 94, 96 are all preferably formed from substantially the same or similar material as the housing 14 of the fat sizing device 10.

The first and second connection members 94, 96 of the emulsification device 90 preferably have substantially the same or similar construction as one another and as the first connection member 20 of the fat sizing device 10. As such, the first connection member 94 has a tube configuration with an open first connection passageway 98 extending through its entirety, thereby providing a continuous central longitudinal fluid flowpath. In particular, the first connection passageway 98 extends from a first end 100 of the first connection member 94 to an opposite second end 102 of the first connection member 94. The first end 100 of the first connection member 94, termed an emulsification device inlet for the unprocessed harvested fat feed, is preferably fitted with a Luer coupler. The first connection member 94 extends away from the body 92 so that the first end 100 is readily accessible to a user of the emulsification device 90.

The first connection passageway 98 opens directly into a body passageway 104 at the second end 102 of the first connection member 94. The body passageway 104 extends through the entirety of the body 92, thereby providing a continuous central longitudinal flowpath. The second connection member 96 similarly has a second connection passageway 106 which extends from a first end 108 of the second connection member 96 to an opposite second end 110 of the second connection member 96. The first end 108 of the second connection member 96, termed an emulsification device outlet for the at least partially emulsified preprocessed harvested fat, is preferably fitted with a Luer coupler. The second connection passageway 106 opens directly into the body passageway 104 at the second end 110 of the second connection member 96.

It is apparent from the above that the first connection passageway 98, body passageway 104 and second connection passageway 106 are aligned in series in fluid communication with one another and, in sum, provide a continuous open longitudinal fluid passageway or flowpath through the entirety of the emulsification device 90, which is termed the emulsification device passageway. The first and second connection passageways 98, 106 preferably have substantially the same diameter as one another while the body passageway 104 has a substantially smaller diameter than the diameter of the first and second connection passageways 98, 106. For example, the diameter of the first and second connection passageways 98, 106 can be in a range from about 1.5 to 3 times greater than the diameter of the body passageway 104. A representative emulsification device have utility herein has a body passageway with a diameter within a range of about 0.1 inches to 0.05 inches.

Although the present invention is not limited to any particular emulsification mechanism, a diameter step-down 112 in the emulsification device passageway of the emulsification device 90 which is the interface between the first connection passageway 98 and body passageway 104 acts as a flow restrictor and is believed to cause the unprocessed harvested fat to undergo turbulence as it passes through the emulsification device passageway in accordance with the description below, thereby effectively emulsifying at least some of the solids found in the unprocessed harvested fat. It is within the purview of one of ordinary skill in the art applying the teaching herein to select an emulsification device for use in the present method from among a plurality of emulsification devices distinguished from one another by the diameters of their body passageways and/or the magnitude of their diameter step-downs.

Although not shown, the first and second reservoirs of the present emulsification system are preferably substantially the same or similar to the syringes employed as the first and second reservoirs 76, 78 in the above-described fat sizing system. However, the first and second reservoirs of the present emulsification system may vary from the first and second reservoirs 76, 78 of the fat sizing system with respect to fluid capacity. For example, it may be preferable for the first and second reservoirs of the present emulsification system to have a smaller fluid capacity than the first and second reservoirs 76, 78 of the fat sizing system, e.g., 20 cc vs. 60 cc, to facilitate emulsification.

A prefiltration step in accordance with the present embodiment comprises connecting the Luer coupler of the first reservoir of the emulsification system, which is preferably initially filled with the unprocessed harvested fat feed, to the Luer coupler at the first end 100 of the first connection member 94 of a first selected emulsification device. The user correspondingly connects the Luer coupler of the second reservoir, which is preferably initially totally empty, to the Luer coupler at the first end 108 of the second connection member 96 of the first selected emulsification device. The user then applies a pressurizing force to the unprocessed harvested fat in the first reservoir preferably by depressing the plunger into the barrel of the syringe which drives the unprocessed harvested fat from the first reservoir through the first end 100 of the first connection member 94 into the emulsification device passageway and, more particularly, through the first connection passageway 98, body passageway 104 and second connection passageway 106 via the diameter step-down 112. The resulting preprocessed harvested fat, which is at least partially emulsified, exits the first selected emulsification device via the first end 108 of the second connection member 98 where the preprocessed harvested fat is collected in the second reservoir, thereby extending the plunger from the barrel of the syringe. The prefiltration step is completed once the first reservoir is totally emptied and/or the second reservoir is filled to capacity.

In accordance with a preferred embodiment, multiple passes of the above-recited prefiltration step are repeated using the same emulsification system and maintaining the first and second reservoirs continuously connected to the first selected emulsification device. Thus, the second reservoir, which is the receiving reservoir in the first pass, i.e., first prefiltration step, becomes the discharging reservoir in the second pass, i.e., second prefiltration step. The first reservoir, which is the discharging reservoir in the first pass, correspondingly becomes the receiving reservoir in the second pass and so on. In the present preferred embodiment about 20-30 repetitive passes of the same prefiltration step are performed on the harvested fat using the first selected emulsification device which preferably has a relatively larger body passageway diameter on the order of about 0.1 inches.

It is further within the scope of the present preferred embodiment to select a second emulsification device which is substantially identical to the first selected emulsification device except that the second emulsification device preferably has a relatively smaller body passageway diameter on the order of about 0.05 inches. After performing the desired number of repetitive passes on the harvested fat using the first selected emulsification device, the first and second reservoirs are disconnected from the first selected emulsification device and reconnected to the second selected emulsification device which is sterile without exposing the harvested fat to the external environment. Any number of passes of the prefiltration step, and preferably 20-30, are performed on the harvested fat using the second selected emulsification device. It bears noting that the above-recited description of the prefiltration steps is provided by way of illustration and is not intended to limit the present invention to any specific number of prefiltration steps performed and/or to any specific number of different emulsification devices selected and used.

Once prefiltration of the harvested fat is completed, the reservoir of the emulsification system containing the preprocessed harvested fat can be connected to the first end 54 of the first connection member 20 of the primed fat sizing device 10, in which case the reservoir of the emulsification system serves as the first or discharging reservoir 76 of the fat sizing system 74. A sterile emulsification device, such as the emulsification device 90 described above, has further utility in association with the second or receiving reservoir 78 of the fat sizing system 74. After completion of the fat sizing procedure and disconnection of the second reservoir 78 from the fat sizing device 10, the Luer coupler of the second reservoir 78 can be connected to one of the Luer couplers of the sterile emulsification device. A Luer coupler of a sterile patient injection syringe (not shown) can also be connected to the other Luer coupler of the sterile emulsification device, thereby enabling closed, anaerobic fluid communication between the second reservoir 78 and patient injection syringe via the emulsification device passageway. The user is able to fill one or more patient injection syringes with sized fat, preferably nanofat, from the filled second reservoir 78 of the fat sizing system 74. It is noted that patient injection syringes are often much smaller than the reservoirs of the fat sizing system 74 and/or the emulsification system to accommodate very fine sharp syringe cannulas on the order of about 27-30 gauge and have much less fluid capacity to accommodate single patient dosages of sized fat, e.g., 1 cc.

It is apparent that the above-described embodiments of the emulsification and sizing systems and their methods of use are all preferably closed and anaerobic.

While the forgoing preferred embodiments of the invention have been described and shown, it is understood that alternatives and modifications, such as those suggested and others, may be made thereto and fall within the scope of the invention.

We claim:
1. A fat sizing device comprising:
   a housing including:
      a cover including a circular enclosing surface from which a tubular sealing lip extends that is aligned circumferentially orthogonal to said enclosing surface, and a first connection member defining an inlet passage attached to said cover;
      a base including:
         a dividing member including a fluid passage extending therethrough;
         an open circular upper end extending from an upper end of said dividing member and defining an upper chamber in fluid communication with said fluid passage, wherein an exterior of said open circular upper end threadably engages an interior of said tubular sealing lip, to enclose said upper chamber;
         an open lower end extending and widening from a lower end of said dividing member to define a lower chamber; and
         a second connection member defining an outlet passage extending therethrough and being in fluid communication with said fluid passage, wherein said second connection member extends from said lower end of said dividing member and is narrower than said open lower end to be situated within said lower chamber; and
      a filter cartridge sealingly situated in said upper chamber between said inlet passage and said fluid passage, such that only material capable of passing through said filter cartridge passes through said upper chamber into said fluid passage.

2. The fat sizing device of claim 1, wherein said filter cartridge includes a first filter element and a second filter element.

3. The fat sizing device of claim 2, wherein said first filter element has an exterior formed from a first material that is different from a second material that forms an exterior of said second filter element.

4. The fat sizing device of claim 3, wherein said first material is a ceramic and said second material is an organic polymer.

5. The fat sizing device of claim 4, wherein said ceramic is titanium nitride.

6. The fat sizing device of claim 4, wherein said organic polymer is a parylene.

7. The fat sizing device of claim 2, wherein said first filter element has a first mesh size and said second filter element has second mesh size different than said first mesh size.

8. The fat sizing device of claim 7, wherein said first mesh size is greater than said second mesh size.

9. The fat sizing device of claim 1, wherein an outside surface of said tubular sealing lip is knurled to facilitate gripping it.

10. The fat sizing device of claim 1, wherein an outside surface of said open lower end is knurled to facilitate gripping it.

11. The fat sizing device of claim 1, wherein said first connection member, is fitted with a Luer coupler for coupling with a syringe.

12. The fat sizing device of claim 1, wherein said second connection member, is fitted with a Luer coupler for coupling with a syringe.

\* \* \* \* \*